(12) United States Patent
Flohr

(10) Patent No.: US 9,125,965 B2
(45) Date of Patent: Sep. 8, 2015

(54) SUPERABSORBENT POLYMERS COMPRISING DIRECT COVALENT BONDS BETWEEN POLYMER CHAIN SEGMENTS AND METHODS OF MAKING THEM

(75) Inventor: Andreas Flohr, Kronberg (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/059,941

(22) Filed: Feb. 17, 2005

(65) Prior Publication Data

US 2005/0203474 A1 Sep. 15, 2005

(30) Foreign Application Priority Data

Feb. 24, 2004 (EP) .................................. 04004132
Jul. 20, 2004 (EP) .................................. 04017070

(51) Int. Cl.
*C08J 3/20* (2006.01)
*A61L 15/60* (2006.01)
*C08J 3/24* (2006.01)
*C08J 3/28* (2006.01)

(52) U.S. Cl.
CPC ................. *A61L 15/60* (2013.01); *C08J 3/245* (2013.01); *C08J 3/28* (2013.01); *C08J 2300/14* (2013.01); *C08J 2333/02* (2013.01)

(58) Field of Classification Search
CPC ........... A61F 5/44; A61F 13/15; A61F 13/53; A61M 1/00; A61M 27/00; A61L 15/60; C08G 85/00; C08J 3/07; C08J 3/075; C08J 3/11; C08J 3/16; C08J 3/24; C08J 3/241; C08J 3/245
USPC ............... 526/232.1, 328; 604/358, 366–368; 522/62, 81
See application file for complete search history.

(56) References Cited

U.S. PATENT DOCUMENTS

| | | | |
|---|---|---|---|
| 3,661,875 A | 5/1972 | Sieja | |
| 3,948,740 A * | 4/1976 | Phalangas | 522/62 |
| 4,043,887 A * | 8/1977 | Pacifici et al. | 522/45 |
| 4,062,817 A | 12/1977 | Westerman | |
| 4,076,663 A | 2/1978 | Masuda et al. | |
| 4,093,776 A | 6/1978 | Aoki et al. | |
| 4,666,983 A | 5/1987 | Tsubakimoto et al. | |
| 4,734,478 A | 3/1988 | Tsubakimoto et al. | |
| 4,839,439 A * | 6/1989 | Mauz | 526/203 |
| 5,137,537 A | 8/1992 | Herron et al. | |
| 5,147,345 A | 9/1992 | Young et al. | |
| 5,164,459 A | 11/1992 | Kimura et al. | |
| 5,196,456 A * | 3/1993 | Nguyen et al. | 522/81 |
| 5,260,345 A | 11/1993 | Desmarais et al. | |
| 5,342,338 A | 8/1994 | Roe | |
| 5,387,207 A | 2/1995 | Dyer et al. | |
| 5,397,316 A | 3/1995 | Lavon et al. | |
| 5,625,222 A | 4/1997 | Yoneda et al. | |
| 5,721,295 A * | 2/1998 | Bruggemann et al. | 524/44 |
| 5,883,158 A | 3/1999 | Nambu et al. | |
| 6,011,196 A * | 1/2000 | Wang et al. | 604/368 |
| 6,130,304 A * | 10/2000 | Sumiya et al. | 526/317.1 |
| 6,565,981 B1 | 5/2003 | Messner et al. | |
| 6,579,958 B2 | 6/2003 | Wilson | |
| 7,166,356 B2 | 1/2007 | Flohr | |

FOREIGN PATENT DOCUMENTS

| | | | | |
|---|---|---|---|---|
| EP | 0248437 A2 * | 6/1987 | ............... | C08K 5/14 |
| EP | 248437 A * | 12/1987 | ............... | C08F 8/00 |
| EP | 0248437 A2 | 12/1987 | | |
| EP | 0509708 B1 | 12/1997 | | |
| EP | 1199327 A2 | 4/2002 | | |
| EP | 1 504 771 A | 2/2005 | | |
| EP | 1 504 772 A | 2/2005 | | |
| EP | 1 506 788 A | 2/2005 | | |
| JP | 63-043930 | 2/1988 | | |
| JP | 01 292103 A | 11/1989 | | |
| WO | WO 96/07380 A1 * | 3/1996 | ............. | A61F 13/15 |
| WO | WO 99/55393 A | 11/1999 | | |
| WO | WO 0189591 A2 | 11/2001 | | |
| WO | WO 0189592 A2 | 11/2001 | | |

OTHER PUBLICATIONS

PCT International Search Report, mailed Jul. 28, 2005 (13 pages).

* cited by examiner

*Primary Examiner* — Melanie Hand
(74) *Attorney, Agent, or Firm* — Andrew J. Mueller; John G. Powell; Andrew A. Paul

(57) ABSTRACT

The present invention relates to superabsorbent polymer particles with improved cross-linking and their use in absorbent articles.
Superabsorbent polymers of the invention comprise polymer chain segments, wherein at least a part of these polymer chain segments are cross-linked to each other through direct covalent bonds.
Moreover, the invention relates to processes for making these superabsorbent polymer particles.

6 Claims, 2 Drawing Sheets

SUPERABSORBENT POLYMERS COMPRISING DIRECT COVALENT BONDS BETWEEN POLYMER CHAIN SEGMENTS AND METHODS OF MAKING THEM

FIELD OF THE INVENTION

The present invention relates to superabsorbent polymers comprising polymer chain segments, which are directly bound to each other through covalent bonds.

Moreover, the invention relates to processes for making these superabsorbent polymer particles and to absorbent articles comprising these superabsorbent polymers.

BACKGROUND OF THE INVENTION

Superabsorbent polymers (SAPs) are well known in the art. They are commonly applied in absorbent articles, such as diapers, training pants, adult incontinence products and feminine care products to increase the absorbent capacity of such products while reducing their overall bulk. The SAPs generally are capable of absorbing and retaining amounts of aqueous fluids equivalent to many times their own weight.

Commercial production of SAPs began in Japan in 1978. The early superabsorbent was a cross-linked starch-polyacrylate. Partially neutralized polyacrylic acid eventually replaced earlier superabsorbents in the commercial production of SAPs, and is the primary polymer employed for SAPs today. They generally consist of a partially neutralized lightly cross-linked polymer network, which is hydrophilic and permits swelling of the network once submerged in water or an aqueous solution such as physiological saline. The cross-links between the polymer chains assure that the SAP does not dissolve in water. SAPs are often applied in form of small particles, such as fibers or granules.

After absorption of an aqueous solution, swollen SAP particles become very soft and deform easily. Upon deformation the void spaces between the SAP particles may be blocked, which drastically increases the flow resistance for liquids. This is generally referred to as "gel-blocking". In gel blocking situations liquid can move through the swollen SAP particles only by diffusion, which is much slower than flow in the interstices between the SAP particles.

One commonly applied way to reduce gel-blocking is to make the particles stiffer, which enables the SAP particles to retain their original shape thus creating or maintaining void spaces between the particles. A well-known method to increase stiffness is to cross-link the carboxyl groups exposed on the surface of the SAP particles. This method is commonly referred to as surface cross-linking.

European Patent EP 0 509 708 B1 refers to surface cross-linked and surfactant coated absorbent resin particles and a method of their preparation. The surface cross-linking agent in EP 0 509 708 B1 is a polyhydroxyl compound comprising at least two hydroxyl groups, which react with the carboxyl groups on the surface of the SAP particles. In EP 0 509 708 B1, surface cross-linking is carried out at temperatures of 150° C. or above. The particles are preferably exposed to the elevated temperatures for at least 5 minutes but less than 60 minutes.

U.S. Pat. No. 5,164,459 discloses another method for surface cross-linking absorbent resins, wherein the carboxyl groups of the polymer, which are comprised on the surface of the resin, react with a polyhydric alcohol. The reaction is accomplished at temperatures in the range of 90° C. to 250° C.

In WO 01/89591 A2 hydroxyalkylurea is used as cross-linking agent. WO 01/89592 applies hydroxyalkylamide as cross-linking agent. In both applications, the surface cross-linking reaction is carried out at temperatures from about 90° C. to about 170° C. for 60 to 180 minutes.

A water-soluble peroxide radical initiator as surface cross-linking agent is known from European Patent Application EP 0 248 437 A2. An aqueous solution containing the surface cross-linking agent is applied on the surface of the polymer. The surface cross-linking reaction is achieved by heating to a temperature such that the peroxide radical initiator is decomposed while the polymer is not decomposed.

European Patent Application EP 1 199 327 A2 discloses the use of an oxetane compound and/or an imidazolidinone compound for use as surface cross-linking agent. The surface cross-linking reaction is carried out under heat, wherein the temperature is preferably in the range of 60° C. to 250° C. Alternatively, the surface cross-linking reaction in EP 1 199 327 A2 is achieved by a photo-irradiation treatment, preferably using ultraviolet rays.

All processes known from the prior art result in surface cross-linked particles, wherein the reaction products of the surface cross-linking molecules are built into the SAP particles. Hence, the surface cross-linked SAP particles comprise the reaction product of the cross-linking molecules.

In general, the surface cross-linking agent is applied on the surface of the SAP particles. Therefore, the reaction preferably takes place on the surface of the SAP particles, which results in improved cross-linking on the surface while not substantially affecting the core of the particles. Hence, the SAP particles become stiffer and gel-blocking is reduced.

A drawback of the commercial surface cross-linking process described above is that it takes a relatively long time, commonly at least about 30 min. However, the more time is required for the surface cross-linking process, the more surface cross-linking agent will penetrate into the SAP particles, resulting in increased cross-linking inside the particles, which has a negative impact on the capacity of the SAP particles. Therefore, it is desirable to have short process times for surface cross-linking. Furthermore, short process times are also desirable with respect to an overall economic SAP particle manufacturing process.

Another drawback of common surface cross-linking processes is that they take place only under relatively high temperatures, often around 150° C. or above. At these temperatures, not only the surface cross-linker reacts with the carboxyl groups of the polymer, but also other reactions are activated, e.g. anhydride-formation of neighboured carboxyl groups within or between the polymer chains, and dimer cleavage of acrylic acid dimers incorporated in the SAP particles. Those side reactions also affect the core, decreasing the capacity of the SAP particles. In addition, exposure to elevated temperatures can lead to colour degradation of the SAP particles. Therefore, these side reactions are generally undesirable.

SAPs known in the art are typically partially neutralized, e.g. with sodium hydroxide. However, in the processes known in the art, neutralization has to be carefully balanced with the need for surface cross-linking: The surface cross-linking agents known in the art only react with free carboxyl groups comprised by the polymer chains but they are not able to react with a neutralized carboxyl groups. Thus, the carboxyl groups can either be applied for surface cross-linking or for neutralization, but the same carboxyl group cannot be applied to fulfil both tasks. Surface cross-linking agents known in the art generally do not react with chemical groups other than carboxyl groups, e.g. they do not react with aliphatic groups.

In the process of making SAP particles, neutralization of free carboxyl groups typically comes first, before surface cross-linking takes place. Indeed, the neutralization step is often carried out in the very beginning of the process, before the monomers are polymerized and cross-linked to form the SAP. Such a process is named 'pre-neutralization process'. Alternatively, the SAP can be neutralized in the middle of polymerization or after polymerization ('post-neutralization'). Furthermore, a combination of these alternatives is also possible.

As the overall number of free carboxyl groups on the outer surface of the SAP particles is limited by the foregoing neutralization, it is very difficult to obtain particles with a high degree of surface cross-linking and hence, a high stiffness to reduce gel-blocking. Furthermore, it is very difficult to obtain SAP particles with evenly distributed surface cross-linking, as the remaining free carboxyl groups are not only few in number but generally also randomly distributed, which sometimes results in SAP particles with regions of rather dense surface cross-linking and regions of sparsely surface cross-linking.

It would be desirable to provide SAP particles, which have a high degree of surface cross-linking and at the same time allow for a high degree of neutralization.

It would also be desirable to provide SAP particles with evenly distributed, homogenous surface cross-linking. It would be beneficial if the surface comprising the surface cross-linking were as thin as possible.

It would be desirable to provide SAPs and SAP particles, wherein the polymer chain segments comprised by the SAPs or SAP particles are cross-linked to each other without the need for a cross-linking molecule being built into the SAPs. This may be desirable with respect to surface cross-linking, i.e. it is desirable to provide surface cross-linked SAP particles, which do not comprise the reaction product of the cross-linking molecules.

Furthermore, it is desirable to provide a process to produce SAPs and SAP particles with the above-mentioned advantages.

It is desirable to provide a process to produce SAP particles, wherein the process step of surface cross-linking can be carried out quickly to increase the efficiency of the process.

Moreover, it is desirable to provide a process to produce SAP particles, which can be carried out at moderate temperatures in order to reduce undesired side reactions, initiated by elevated temperatures, such as anhydride-formation and dimer cleavage.

SUMMARY OF THE INVENTION

The present invention refers to superabsorbent polymers comprising polymer chain segments. At least a part of the polymer chain segments are cross-linked to each other through covalent bonds, wherein the covalent bonds are formed directly between between polymer chain segments.

The present invention further relates to a method of cross-linking superabsorbent polymers, the method comprising the steps of
a) providing a superabsorbent polymer comprising polymer chain segments, and
b) providing a mono-functional radiation activatable radical former, and
c) exposing the superabsorbent polymer and the mono-functional radiation activatable radical former to electromagnetic irradiation, thereby forming direct covalent bonds between the polymer chain segments.

Moreover, the present invention refers further to another method of making superabsorbent polymers which comprises the steps of
a) providing a superabsorbent polymer comprising polymer chain segments, and
b) exposing the superabsorbent polymer to electromagnetic irradiation, preferably electron-beam, thereby forming direct covalent bonds between the polymer chain segments.

Furthermore, the present invention relates to absorbent articles comprising superabsorbent polymer particles comprising direct covalent bonds between polymer chain segments.

BRIEF DESCRIPTION OF THE DRAWINGS

While the specification concludes with claims pointing out and distinctly claiming the present invention, it is believed the same will be better understood by the following drawings taken in conjunction with the accompanying specification wherein like components are given the same reference number.

DETAILED DESCRIPTION OF THE INVENTION

Figure 1:
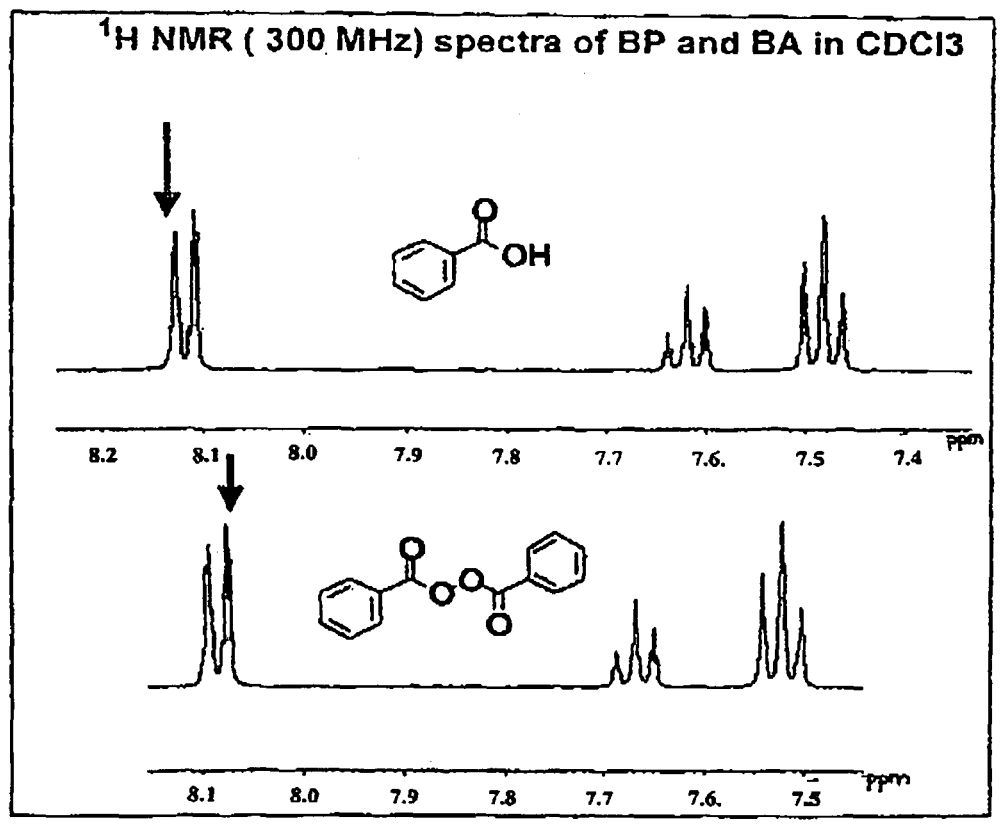
FIG. 1 shows the 300 MHz 1H-NMR spectrum of dibenzoyl peroxide (BP) and benzoic acid (BA).

SAPs are available in a variety of chemical forms, including substituted and unsubstituted natural and synthetic polymers, such as carboxymethyl starch, carboxymethyl cellulose, and hydroxypropyl cellulose; nonionic types such as polyvinyl alcohol, and polyvinyl ethers; cationic types such as polyvinyl pyridine, polyvinyl morpholinione, and N,N-dimethylaminoethyl or N,N-diethylaminopropyl acrylates and methacrylates, and the respective quaternary salts thereof. Typically, SAPs useful herein may have a multiplicity of anionic, functional groups, such as sulfonic acid, and more typically carboxyl groups. Examples of polymers suitable for use herein may include those, which are prepared from polymerizable, unsaturated, acid-containing monomers. Thus, such monomers include the olefinically unsaturated acids and anhydrides that contain at least one carbon-to-carbon olefinic double bond. More specifically, these monomers can be selected from olefinically unsaturated carboxylic acids and acid anhydrides, olefinically unsaturated sulfonic acids, and mixtures thereof.

Some non-acid monomers can also be included, usually in minor amounts, in preparing SAPs. Such non-acid monomers can include, for example, the water-soluble or water-dispersible esters of the acid-containing monomers, as well as monomers that contain no carboxylic or sulfonic acid groups at all. Optional non-acid monomers can thus include monomers containing the following types of functional groups: carboxylic acid or sulfonic acid esters, hydroxyl groups, amide-groups, amino groups, nitrile groups, quaternary ammonium salt groups, aryl groups (e.g., phenyl groups, such as those derived from styrene monomer). These non-acid monomers are well-known materials and are described in greater detail, for example in U.S. Pat. No. 4,076,663 and in U.S. Pat. No. 4,062,817.

Olefinically unsaturated carboxylic acid and carboxylic acid anhydride monomers may include the acrylic acids typified by acrylic acid itself, methacrylic acid, ethacrylic acid, α-chloroacrylic acid, a-cyanoacrylic acid, β-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-sterylacrylic acid, itaconic acid, citroconic acid, mesaconic acid, glutaconic acid, aconitic acid, maleic acid, fumaric acid, tricarboxyethylene and maleic acid anhydride.

Olefinically unsaturated sulfonic acid monomers may include aliphatic or aromatic vinyl sulfonic acids such as vinylsulfonic acid, allyl sulfonic acid, vinyl toluene sulfonic acid and styrene sulfonic acid; acrylic and methacrylic sulfonic acid such as sulfoethyl acrylate, sulfoethyl methacrylate, sulfopropyl acrylate, sulfopropyl methacrylate, 2-hydroxy-3-methacryloxypropyl sulfonic acid and 2-acrylamide-2-methylpropane sulfonic acid.

SAPs that may be useful for the present invention may comprise carboxyl groups. These polymers may comprise hydrolyzed starch-acrylonitrile graft copolymers, partially neutralized hydrolyzed starch-acrylonitrile graft copolymers, starch-acrylic acid graft co-polymers, partially neutralized starch-acrylic acid graft copolymers, saponified vinyl acetate-acrylic ester copolymers, hydrolyzed acrylonitrile or acrylamide copolymers, slightly network crosslinked polymers of any of the foregoing copolymers, partially neutralized polyacrylic acid, and slightly network crosslinked polymers of partially neutralized poly-acrylic acid, partially neutralized polymethacrylic acid, and slightly network crosslinked polymers of partially neutralized polymethacrylic acid. These polymers can be used either solely or in the form of a mixture of two or more different polymers, that when used as mixtures, individually do not have to be partially neutralized, whereas the resulting copolymer has to be. Examples of these polymer materials are disclosed in U.S. Pat. No. 3,661,875; U.S. Pat. No. 4,076,663; U.S. Pat. No. 4,093,776; U.S. Pat. No. 4,666,983; and U.S. Pat. No. 4,734,478.

The SAPs useful for the present invention preferably may comprise a homopolymer of partially neutralized α,β-unsaturated carboxylic acid or a copolymer of partially neutralized α,β-unsaturated carboxylic acid copolymerized with a monomer copolymerizable therewith.

A suitable method for polymerizing monomers may be aqueous solution polymerization. An aqueous solution comprising monomers and polymerization initiator is subjected to a polymerization reaction. The aqueous solution may comprise e.g. α,β-unsaturated carboxylic acid monomers, or may, alternatively, comprise α,β-unsaturated carboxylic acid monomers and additional monomers, which are co-polymerizable with the α,β-unsaturated carboxylic acid monomers. At least the α,β-unsaturated carboxylic acid should be partially neutralized, either prior to polymerization of the monomers, during polymerization or after polymerization. In case the α,β-unsaturated carboxylic acid is partially neutralized prior to polymerization, the monomers (including α,β-unsaturated carboxylic acid monomers and possible comonomers) are at least about 50% neutralized. In another embodiment, the monomers may be at least about 70% neutralized and may be at least about 75% neutralized in yet another embodiment. In another embodiment, the monomers may be from about 75% to about 95% neutralized.

The monomers in aqueous solution are polymerized by standard free radical techniques, commonly by using a photoinitiator for activation, such as ultraviolet (UV) light. Alternatively, a redox initiator may be used. In this case, however, increased temperatures may be necessary.

The polymer chains may be lightly cross-linked to render them water-insoluble. The cross-linked structure may be obtained by the co-polymerization of the selected water-soluble monomer and a cross-linking agent possessing at least two polymerizable double bonds in the molecular unit. The cross-linking agent may be present in an amount effective to cross-link the water-soluble polymer. The amount of cross-linking agent may be determined by the desired degree of absorption capacity and the desired strength to retain the absorbed fluid, that is, the desired absorption under load. Typically, the cross-linking agent may be used in amounts ranging from 0.0005 to 5 parts by weight per 100 parts by weight of monomers (including α,β-unsaturated carboxylic acid monomers and possible co-monomers) used. If an amount over 5 parts by weight of cross-linking agent per 100 parts is used, the resulting polymer may have too high cross-linking density and may exhibit reduced absorption capacity and increased strength to retain the absorbed fluid. If the cross-linking agent is used in an amount less than 0.0005 parts by weight per 100 parts, the polymer may have too low cross-linking density and when contacted with the fluid to be absorbed may become rather sticky, water-soluble and may exhibit a low absorption performance, particularly under load. The cross-linking agent may be soluble in the aqueous solution.

Alternatively to co-polymerizing the cross-linking agent with the monomers, it may also be possible to cross-link the polymer chains in a separate process step after polymerization.

After polymerization, cross-linking and partial neutralization, the viscous SAPs are dehydrated (i.e. dried) to obtain dry SAPs. The dehydration step can be performed by heating the viscous SAPs to a temperature of about 120° C. for about 1 or 2 hours in a forced-air oven or by heating the viscous SAPs overnight at a temperature of about 60° C. The content of residual water in the dehydrated SAP after drying predominantly depends on dyring time and temperature and can range from 0.5% by weight of dry SAP up to 50% by weight of dry SAP. In one embodiment, the content of residual water in the dehydrated SAP after drying may be from about 0.5% to about 45% by weight of dry SAP. In another embodiment, the content of residual water in the dehydrated SAP after drying may be about 0.5% to about 30% and in yet another embodiment from about 0.5% to about 15%. In a further embodiment the content of residual water in the dehydrated SAP may be from about 0.5% to about 5%.

The SAPs can be transferred into particles of numerous shapes. The term "particles" refers to granules, fibers, flakes, spheres, powders, platelets and other shapes and forms known to persons skilled in the art of SAPs. The particles can be in the form of granules or beads, having a particle size of about 10 to about 1000 μm, and in another embodiment from about 100 to about 1000 μm. In another embodiment, the SAPs can be in the shape of fibers, i.e. elongated, acicular SAP particles. In those embodiments, the SAP fibers may have a minor dimension (i.e. diameter of the fiber) of less than about 1 mm, in another embodiment less than about 500 μm, and in yet another embodiment less than about 250 μm down to about 50 μm. The length of the fibers may be about 3 mm to about 100 mm. The fibers can also be in the form of a long filament that can be woven.

The present invention relates to SAPs comprising polymer chain segments, wherein at least a part of said polymer chain segments may be cross-linked to each other through covalent bonds formed directly between the polymer chain segments.

A "direct covalent bond" according to the present invention is a covalent bond wherein polymer chains are bound to each other only via a covalent bond with no intermediate atoms, such as atoms comprised by a cross-linking molecule. On the contrary, known cross-linking reactions between polymer chains always result in covalent bonds between these polymer chains, wherein the reaction product of the cross-linking molecule is built in between the polymer chains. Thus, known cross-linking reactions do not result in a direct covalent bond but in an indirect covalent bond comprising the reaction product of the cross-linking molecule. The direct covalent bond is formed between a carbon atom in the backbone of a first polymer chain and a carbon atom in the backbone of a second polymer chain. The bonds are formed intra-particulate within the SAP polymer, more specifically, they are formed on the surface of the SAP particles, while the core of the SAP particles is substantially free of such direct covalent bonds.

The method of making such SAPs can be applied on polymer chains, which have not been cross-linked to each other. Hence, the polymer chains may be provided as a plurality of polymer chains, wherein the polymer chains may at least partially be branched.

Alternatively, the method can be applied for polymer chains, which have already been cross-linked by a cross-linker known in the art, comprising at least two polymerizable double bonds in the molecule unit. The method can be applied polymer chains comprised by SAP particles, e.g. for surface cross-linking. However, the direct covalent bonds between polymer chain segments according to the present invention are not intended to bond different SAP particles to each other. Thus, the method of the present invention, when applied on SAP particles, may not lead to any appreciable inter-particulate direct covalent bonds between different SAP particles but may only result in intra-particulate direct covalent bonds within an SAP particle. If present, such interparticulate direct covalent bonds may hence require additional inter-particulate cross-linking materials, such as cross-linking molecules.

For applications, wherein the polymer chains have already been cross-linked and are thus provided in form of a network, the term "polymer chain segment" refers to the part of the polymer chains between two neighbouring, existing cross-links or to the part of the polymer chains between sites, where the polymer chain is branched.

However, if the polymer chains have not been pre-cross-linked at all prior to subjecting them to the cross-linking process of the present invention, the term "polymer chain segments" refers to a complete individual polymer chain.

In an embodiment of the present invention, the polymer chain segment comprises polycarboxylic acid units. According to the present invention, the term "polycarboxylic acid unit" refers to a unit consisting of at least two carboxylic acid monomer units, which have been polymerized to each other and which are part of a larger polymer. The term "carboxylic acid monomer units" refers to the reaction product of the carboxylic acid monomer after the polymerization reaction and thus refers to the carboxylic acid monomer built into the polymer. In one embodiment of the present invention, the polycarboxylic acid units consist of polyacrylic acid units or of polymethacylic acid units. A polyacrylic acid unit consists of at least two acrylic acid monomer units, which have been polymerized to each other. A polymethacrylic acid unit consists of at least two methacrylic acid monomer units, which have been polymerized to each other. Alternatively, the carboxylic acid unit may also consist of acrylic acid monomers units and methacylic acid monomers units, which have been copolymerized.

According to the present invention, the polycarboxylic acid units are at least partially neutralized, i.e. at least a part of the carboxylic acid units are neutralized.

Additional to the polycarboxylic acid units, the polymer chain segments may further comprise other units, such as polystyrene units. According to the present invention, the term "polystyrene unit" refers to a unit consisting of at least two styrene monomer units, which have been polymerized to each other and which are part of a larger polymer. The term "styrene monomer units" refers to the reaction product of the styrene monomer after the polymerization reaction and thus refers to the styrene monomer built into the polymer.

The polymer chain segment comprising e.g. polycarboxylic acid units in combination with other polymer units, such as polystyrene units is referred to as a "block polymer chain segment".

Many polymers for use herein are slightly network crosslinked polymers of partially neutralized polyacrylic acids, slightly network crosslinked polymers of partially neutralized polymethacrylic acids, their copolymers and starch derivatives thereof. SAPs may comprise partially neutralized, slightly network crosslinked, polyacrylic acid (i.e. poly (sodium acrylate/acrylic acid)). The SAPs may be at least about 50% neutralized. In one embodiment, the SAPs may be at least about 70% neutralized. In another embodiment the SAPs may be at least about 75% neutralized and in a further embodiment the SAPs may be from about 75% to about 95% neutralized. Network cross-linking renders the polymer substantially water-insoluble and, in part, determines the absorptive capacity of the hydrogel-forming absorbent polymers. Processes for network cross linking these polymers and typical network cross linking agents are described in greater detail in U.S. Pat. No. 4,076,663.

In another embodiment of the present invention, the method of directly bonding polymer chain segments to each other by a covalent bond may be applied for surface cross-linking SAP particles instead of or additional to conventional surface cross-linking.

According to the present invention, such direct covalent bonds can be introduced by two different methods: One method applies electromagnetic irradiation together with radical former molecules and the second method only applies electromagnetic irradiation without the need for any further chemicals, such as radical former molecules, to initiate cross-linking. In case only electromagnetic irradiation is used to generate direct covalent bonds, such electromagnetic irradiation has to be much more powerful than in case electromagnetic irradiation plus radical former molecules are used. This, in turn, can lead to back-bone polymer chain degradation in the SAP (chain sessioning). Hence, in case only electromagnetic irradiation is used, within the SAP new covalent bonds may be generated and existing covalent bonds may be broken. Therefore, the e-beam dosage (depending e.g. on the e-beam intensity and time of exposure) has to be chosen in a way that such ratio is in favour of creating more bonds than breaking existing ones upon irradiation.

a) Use of radical former molecules (hereinafter referred to as radical formers) together with electromagnetic irradiation:

It has been found that a radical former comprising one radiation activatable group, upon activation by electromagnetic irradiation can abstract a hydrogen radical from a polymer chain segment. Two of those radicals induced in the polymer chain segments can combine to form a direct covalent bond between polymer chain segments. According to the present invention, a radical former comprising only one radiation activatable group is mono-functional.

Preferred mono-functional radical formers according to the present invention may include, but are not limited to, dialkyl peroxy-dicarbonates, benzilketales, di-tert-butyl peroxide, di-benzoyl peroxide, bis-(aroyloxyl) peroxides such as bis-(4-methoxy) di-benzoyl peroxide, or bis-(4-methyl) di-benzoyl peroxide, or bis-(4-chloro) di-benzoyl peroxide, 2,4,6-tri-methyl di-benzoyl peroxide, 3-benzoyl benzoic acid, 1,3-diibenzoyl propane, trifluoromethyl phenylketone, acetophenone, benzophenone, terephthalophenone, fluorenone, xanthone, thio-xanthone, anthraquinone, benzil, α-ketocoumarins, camphorquinone, α-alkoxydeoxybenzoins, α,α-dialkyloxydeoxybenzoins, α,α-dialkoxyacetophenones, α,α-hydroxyalkylphenones, O-acyl α-oximinoketones, di-benzoyl disulphide, S-phenyl thiobenzoates, acylphosphine oxides, benzoylphosphineoxides, aryl-aryl-sulphides, di-benzoyl methanes, phenylazo-di-phenyl sulphone, substituted dialkyl peroxy-dicarbonates, substituted benzilketales, substituted di-tert-butyl peroxides, substituted di-benzoyl peroxides, substituted bis-(aroyloxyl) peroxides such as substituted bis-(4-methoxy) di-benzoyl peroxide, or substituted bis-(4-methyl) di-benzoyl peroxide, or substituted bis-(4-chloro) di-benzoyl peroxide, substituted 2,4,6-tri-methyl di-benzoyl peroxide, substituted 3-benzoyl berizoic acid, substituted 1,3-diibenzoyl propane, substituted trifluoromethyl phenylketone, substituted acetophenones, substituted benzophenones, substituted terephthalophenones, substituted fluorenones, substituted xanthones, substituted thio-xanthones, substituted anthraquinones, substituted benzils, substituted α-ketocoumarins, substituted camphorquinones, substituted α-alkoxydeoxybenzoins, substituted α,α-dialkyloxydeoxybenzoins, substituted α,α-dialkoxyacetophenones, substituted α,α-hydroxyalkylphenones, substituted O-acyl α-oximinoketones, substituted di-benzoyl disulphide, substituted S-phenyl thiobenzoates, substituted acylphosphine oxides, substituted benzoylphosphineoxides, substituted aryl-aryl-sulphides, substituted di-benzoyl methanes, substituted phenylazo-di-phenyl sulphone, In a preferred embodiment of the invention, such derivatization is done to either enable or further enhance water-solubility.

In the following, the reactions potentially taking place when applying a mono-functional radical former to polymer chain segments is exemplarily depicted for di-benzoyl peroxide as radical former and for polymer chain segments comprising polyacrylic acid units (PAA):

1) Upon UV initiation, the di-benzoyl peroxide forms benzoyl benzoic acid radicals according to Formula 1a.

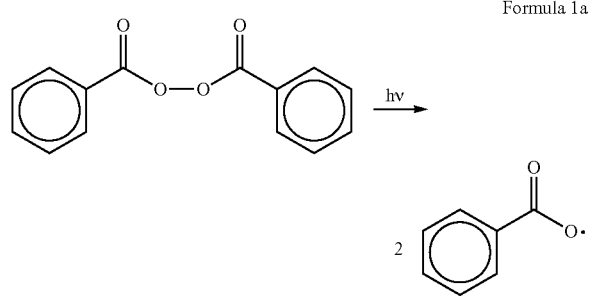

Formula 1a

The benzoic acid radical may theoretically de-carboxylate to form benzene radicals as depicted in Formula 1b.

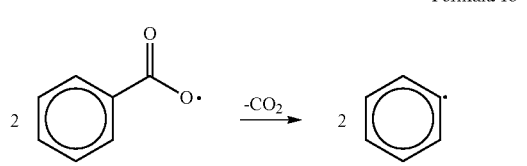

Formula 1b

After this initial reaction, all of the following reactions 2) to 9) may theoretically take place:

2) The benzoyl benzoic acid radicals can recombine to again form di-benzoyl peroxide as depicted in Formula 2.

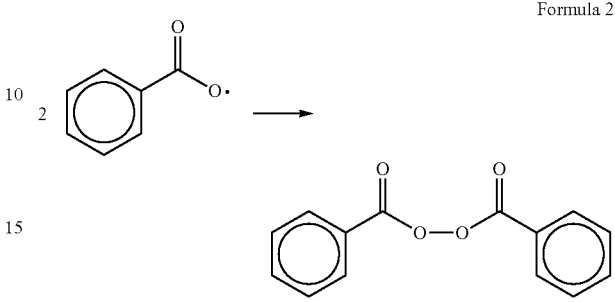

Formula 2

3) Alternatively to the reaction of Formula 2, the benzoyl benzoic acid radical can react with the benzene radical to form the corresponding ester, according to Formula 3.

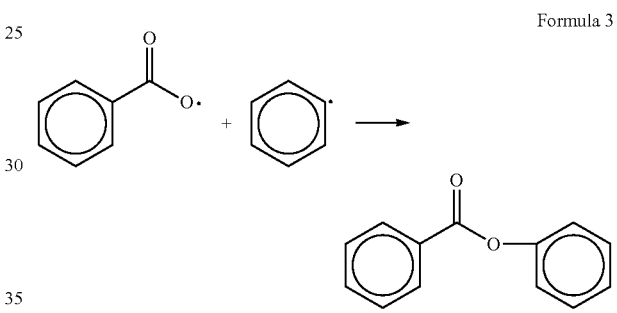

Formula 3

4) Also, a recombination of two benzene radicals to form bi-phenyl as in Formula 4 is theoretically possible.

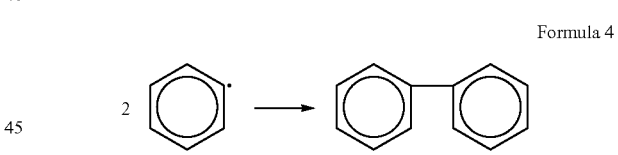

Formula 4

5) As a further alternative, the benzoyl benzoic acid radical can react with the PAA to form benzoic acid and a PAA-radical, according to Formula 5.

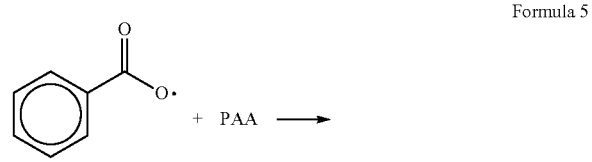

Formula 5

The benzoic acid may be subjected to an oxidative reaction to regenerate the radical former di-benzoyl peroxide.

6) Furthermore, benzene radicals, if formed, could also react with the PAA according to Formula 6 to form benzene and a PAA-radical.

Formula 6

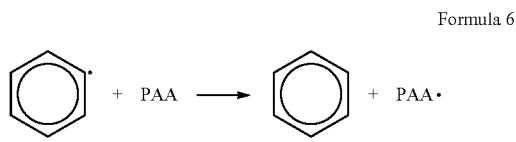

If PAA-radicals according to Formula 5 and 6 have been formed, the following reactions comprising PAA-radicals may principally take place:
7) The PAA-radical can, in turn, react again with the benzoyl benzoic acid radical, whereby the benzoyl benzoic acid radical is attached to the PAA polymer chain segment as depicted in Formula 7.

Formula 7

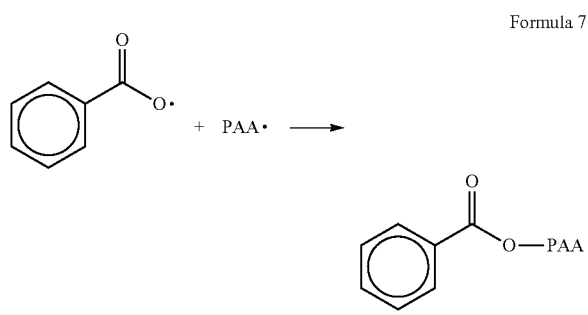

8) Alternatively, the PAA-radical can react with the benzene radical to attach the benzene radical to the polymer chain as depicted in Formula 8.

Formula 8

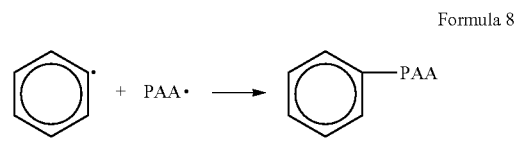

9) As a second alternative, two PAA-radicals can recombine, according to Formula 9.

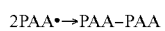

Formula 9:

The reaction according to Formula 9 results in polymer chain segments, which are directly covalently bound to each other.

To determine, which of the above reactions have actually taken place, the reaction samples may be extracted with ether after UV initiation, and the extracts may be analysed via $^1$H-NMR and $^{19}$F-NMR (for example in case tri-fluoromethyl phenylketone is used as radical former). FIG. 1 depicts the 300 MHz $^1$H-NMR spectra of di-benzoyl peroxide (BP) and benzoic acid (BA).

Figure 2:
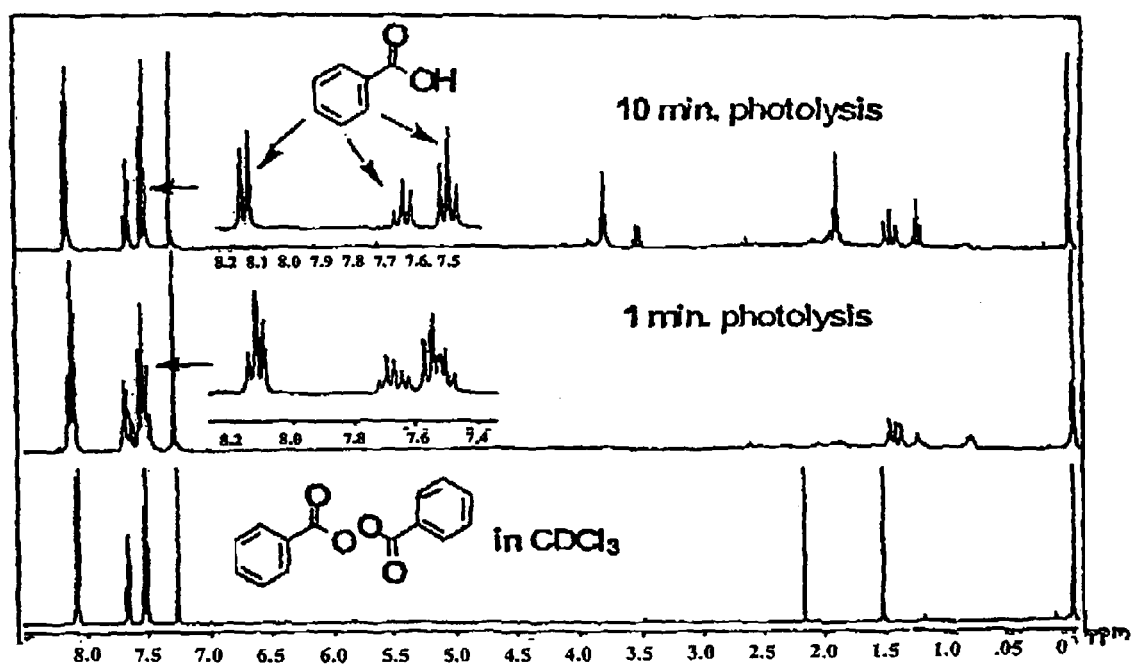
FIG. 2 shows the $^1$H-NMR spectrum of the ether extract before photolysis, after 1 minute photolysis and after 10 minutes photolysis.

In the above-mentioned example where the radical former is di-benzoyl peroxide, the $^1$H-NMR spectra of the ether extract may reveal the presence of benzoic acid, according to FIG. 2. Benzoic acid may be formed in the reaction according to Formula 5. Moreover, the reaction according to Formula 5 may take place if the benzoyl benzoic acid radicals are generated according to Formula 1a. Hence, the ether extract may show that the reactions as depicted in Formula 1a and 5 may take place. Thus, PAA-radicals according to Formula 5 may form.

The esther according to Formula 3 may not be detected in the ether extract. Additionally, the bi-phenyl as a reaction product of the reaction according to Formula 4, or the reaction products of Formula 7 or Formula 8 may not be found in the ether extract. If that is the case, reactions involving benzene radicals may not take place. Consequently, no benzene radicals according to Formula 1b may be formed.

Accordingly, as the $^1$H-NMR spectra of FIG. 2 derived from the ether extracts may show that out of the reactions depicted in Formulae 1 to 8, only the reactions of Formula 1a, Formula 5 and possibly Formula 2 (recombination of the radical former) may actually take place, the reaction of Formula 9 may also takes place. The PAA-radicals, which are formed as depicted in Formula 5 may not react with the benzoyl benzoic acid radicals according to Formula 7 and they may not react with the benzene radical according to Formula 8. However, as free radicals may not be stable and no other reaction partner may be available, the PAA-radicals may have recombined according to the reaction depicted in Formula 9. Thus, a direct covalent bond between different polymer chain segments may have been built.

This direct bond cannot comprise the reaction product of the radical former because the radical former may only comprise one radiation activatable group and thus might not be able to form a cross-link upon UV irradiation as this would require at least two radiation activatable groups. Consequently, when applying di-benzoyl peroxide as radical former to polymer chain segments comprising polyacrylic acid (PAA) and subsequently UV initiating the di-benzoyl peroxide, the following reaction takes place:

Formula 10

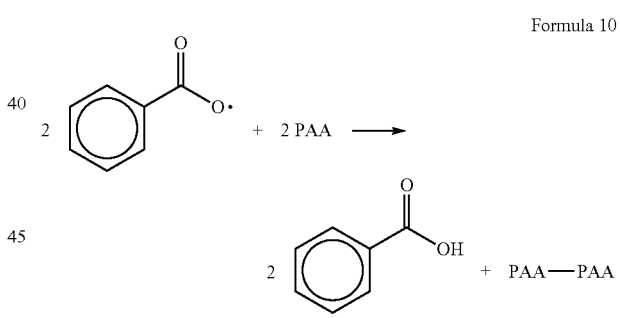

Cross-linkers known in the art had to be at least bi-functional to be able to covalently cross-link different polymer chain segments to each other: Examples are the thermally activated surface cross-linkers such as di- or polyhydric alcohols, or derivatives thereof, as discussed above.

Contrary thereto, the radical formers of the present invention may be mono-functional. The radical formers may form radicals upon exposure to electromagnetic irradiation. Electron beams as well as UV-light can produce suitable electromagnetic irradiation. UV-light may be used with a wavelength of 220-380 nm, depending on the selected radical former(s). The UV-light may be used in combination with an electron-beam, and may also be used in combination with an IR-light. In case of combination of UV-irradiation with other electromagnetic irradiation is used, it is not critical if the application of the UV-light takes place simultaneously with the other electromagnetic irradiation (i.e. electron-beam or IR-light), or if irradiation is done in a series of different irradiation steps. For radical formers, which require a relative high amount of activation energy, activation with electron beams may be necessary.

The UV irradiation can be carried out in a conventional manner with UV lamps having a power between about 50 W and about 2 kW, in another embodiment between about 200 W and about 700 W, and in yet another embodiment between about 400 W and about 600 W. Irradiation time may be between about 0.1 sec. and about 30 min., in another embodiment between about 0.1 sec. and about 15 min, in yet another embodiment between about 0.1 sec. and about 5 min and in a further embodiment between about 0.1 sec. and about 2 min. Commercially available mercury pressure UV-lamps can be used. The choice of the lamp may depend on the absorption spectrum of the radical former(s) used. Lamps having a higher power generally permit more rapid cross-linking. The distance between the UV-lamp(s) and the SAP which is to be cross-linked preferably varies between 5 cm and 15 cm.

Upon electromagnetic irradiation, such as UV irradiation, the radical formers may form free radicals. The highly reactive free radicals formed thereby may react with polymer chain segments comprised by the superabsorbent polymer. When a free radical formed from the radical former reacts with a polymer chain segment, the polymer chain segment may form a "polymer chain segment radical". It is believed that reaction within the polymer chain segment takes place on an aliphatic group (C—H group) comprised by the polymer chain segment. Alternatively, the reaction may also take place on those carboxylic groups comprised by the polymer chain segment, which have not been neutralized. A further alternative is that the reaction may take place on another functional group comprised by the polymer chain segment if the functional group comprises a Hydrogen radical that can be abstracted. Examples of such functional groups include, but are not limited to, sulfonic acid, carboxylic acid or sulfonic acid esters, hydroxyl groups, amide-groups, amino groups, nitrile groups, quaternary ammonium salt groups, aryl groups (e.g., phenyl groups, such as those derived from styrene monomer). When two such polymer chain segment radicals react with each other, a direct covalent bond between the polymer chain segments may be formed.

It is believed that the reaction which leads to direct covalent bonds between polymer chain segments preferably takes place on molecules comprised by the polymer backbone. Radical formers according to the present invention may have a molecular weight of at least about 25 g/mol, in another embodiment at least about 60 g/mol, in yet another embodiment at least about 120 g/mol, in still another embodiment at least about 180 g/mol and in a further embodiment at least about 240 g/mol. Radical formers having a relatively high molecular weight often tend to form more stable radicals, as the charge of the radical can be distributed better within the radical. Hence, the radical may be more likely to reach a polymer chain segment within the reaction solution and may be able to react with the polymer chain segment to form a "polymer chain segment radical". If the radical were very unstable, it would more likely react to recombine to the radical former as depicted in Formula 2.

Furthermore, radical formers according to the present invention may comprise aromatic groups, such as arenes. This may also lead to more stable radicals as the charge can be distributed throughout the aromatic group.

b) Use of electron beam only (no use of additional chemicals to initiate cross-linking is required)

Upon electromagnetic irradiation, radicals may be formed in the backbone polymer chain of the superabsorbent polymer. Such highly reactive radicals formed thereby may be able to react with polymer chain segments comprised by other chains of the same superabsorbent polymer. The electron-beam may induce a free radical in the polymer chain, hence a "polymer chain segment radical" may be formed. If two such "polymer chain segment radicals" react with each other (according to the reaction depicted in Formula 9 above), a direct covalent bond between tow polymer chain segments may be introduced.

It is well established that atoms are composed of hydrogen radicals and neutrons which are located in the nucleus, as well as negatively charged electrons, which are much lighter and orbit the nucleus. Because they are light and only loosely attracted to the nucleus, electrons can be separated from the atom relatively easy, accelerated using magnetic and electric fields, and focused into a beam of energy. This resultant beam can then be scanned by means of an electromagnet to produce a "curtain" of accelerated electrons. The beam's strength and the amount of energy that it can deposit onto a target are determined by the difference in voltage between the cathode, where the electrons are released, and the positively charged anode which accelerates the electrons, as well as by the current, which is defined as the number of electrons in the beam which pass through a given area per second. For example, the tube inside a TV set accelerates electrons to 20,000 volts, whereas modern industrial accelerators can boost electron energies up to 10,000,000 volts.

In one embodiment of the present invention electron-beam irradiation may be used to have highly energetic electrons strike at or near the carbon-hydrogen bonds in the back-bone polymer of SAP, and give up enough energy to the molecules to break some of the bonds, releasing corresponding low molecular weight degradation products and leaving the SAP with excited carbon atoms (free radicals). When this process occurs at two adjacent polymer chain segments, excited carbon atoms can release excitation energy forming a chemical bond, referred to as a cross-link, between them. The amount of electron beam irradiation absorbed by the SAP is referred to as the dose, which is typically defined in terms of kiloGrays (where 1 kGy=1000 J/kg) or MegaRads (where 1 MRad=1,000,000 erg/g). Electrons will lose some of their energy due to interaction with air, which is why most electron beams operate in a vacuum.

Unlike gamma irradiation, which involves the use of a radioactive Cobalt or Cesium source, e-beam technology neither produces nor stores any irradiation in the target materials once those materials are outside of the beam.

Surface cross-linking of SAPs by means of e-beam processing can be performed using commercially-available accelerators, which are equipped with a variety of material handling systems, and are capable of significant throughput. A typical direct-current accelerator consists of the voltage generator, the electron gun, the accelerator tube, the scan horn, and the control system. This accelerator may create a beam of electrons approximately 2.5 centimeter in diameter and may energize it to near light speed. The beam may pass through a scan horn, where a magnet may scan it back and forth at ca. 200 Hz, creating a curtain of electrons 1-2 meters wide. Target materials may be passed under the scan horn using conveyors, carts, reel-to-reel equipment, or other specialized handling means. Worldwide, there are approximately 700-800 electron beam accelerators in industrial use today. Accelerators are typically described in terms of their energy and power. Low-energy accelerators range from 150 keV to 2.0 MeV. Medium-energy accelerators have energies between 2.5 and 8.0 MeV. High-energy accelerators have beam energies above 9.0 MeV. The beam energy required depends directly on the application for it is to be used. For cross-linking of SAPs accelerators with energies of 150 keV up to 5.0 MeV can be used. Accelerator power is a product of electron energy and beam current. Available beam powers range from 5 to about 300 kW. For example a 5.0 MeV accelerator at 30 mA will have the power of 150 kW.

Accelerators can generally be classified according to exactly how they generate accelerated electrons. The five main types of accelerators are: electrostatic direct-current (DC), electro-dynamic DC, radio-frequency (RF) linear accelerators (LINACS), magnetic-induction LINACs, and continuous-wave (CW) machines.

In general, DC accelerators are characterized by high power output and high efficiency, while LINAC systems are typically much more compact and can generate higher beam energies. However, they are also considerably less efficient. Similarly, CW machines can be fairly compact, and can achieve high beam energies. Regardless of the exact nature of the accelerator, in all EBP facilities, the target materials are passed under the accelerator's scan-horn using conveyors, carts, reel-to-reel equipment, or other specialized handling means. Worldwide, there are approximately 700-800 electron beam accelerators in industrial use today.

With respect to processing economics, e-beam processing typically requires lower energy expenditure than conventional thermo-chemical processes to produce the same net effects.

According to the present invention the dehydrated SAP particles may undergo a surface cross-linking process step. The term "surface" describes the outer-facing boundaries of the particle. For porous SAP particles, exposed internal surfaces may also belong to the surface. The term "surface cross-linked SAP particle" refers to an SAP particle having its polymer chain segments present in the vicinity of the particle surface cross-linked to each other. It is known in the art to surface cross-link the polymer chain segments present in the vicinity of the particle surface by a compound referred to as surface cross-linker. The surface cross-linker may be applied to the surface of the particle. In a surface cross-linked SAP particle the level of cross-links in the vicinity of the surface of the SAP particle may generally be higher than the level of cross-links in the interior of the SAP particle.

Commonly applied surface cross-linkers may be thermally activated surface cross-linkers. The term "thermally activated surface cross-linkers" refers to surface cross-linkers, which only react upon exposure to increased temperatures, typically around 150° C. Thermally activated surface cross-linkers known in the prior art are e.g. di- or polyfunctional agents that are capable of building additional cross-links between the polymer chains of the SAPS. Other thermally activated surface cross-linkers include, e.g., di- or polyhydric alcohols, or derivatives thereof, capable of forming di- or polyhydric alcohols. Representatives of such agents include alkylene carbonates, ketales, and di- or polyglycidlyethers. Moreover, (poly) glycidyl ethers, haloepoxy compounds, polyaldehydes, polyoles and polyamines are also well known thermally activated surface cross-linkers. The cross-linking may be based on a reaction between the functional groups comprised by the polymer, for example, an esterification reaction between a carboxyl group (comprised by the polymer) and a hydroxyl group (comprised by the surface cross-linker). As typically a relatively big part of the carboxyl groups of the polymer chain segments is neutralized prior to the polymerization step, commonly only few carboxyl groups are available for this surface cross-linking process known in the art. For example, in a 70% percent neutralized polymer only 3 out of 10 carboxylic groups are available for covalent surface cross-linking.

According to the present invention, surface cross-linking does not have to comprise a surface cross-linker, the reaction product of which will be built into the SAP particle after surface cross-linking. On the contrary, according to the present invention, it may be possible to surface cross-link the polymer chain segments by directly bonding the polymer chain segments to each other through a covalent bond. The radical former, which initiates the reaction, may not get built in the SAP particle. Optionally, the final reaction product of the radical former can be regenerated after surface cross-linking and hence, after regeneration, can be used again for surface cross-linking. Additional monomers, such as carboxylic acids or styrenes, may not be required if the radical former is used for surface cross-linking of SAP particles.

The direct covalent bonds introduced between polymer chain segments on the surface of the SAP particles according to the present invention may be formed intra-particulate. They may not form inter-particle bonds.

Further, if the radical former is used for surface cross-linking of SAP particles, the radical former may be sprayed onto the SAP particles by means of a fluidized-bed spraying chamber. Simultaneously IR-irradiation may be applied to accomplish drying and simultaneously UV-light may be applied to accomplish cross-linking in the fluidized-bed.

However, in certain cases drying and cross-linking may take place in two steps in series, which could be carried out in any order. Instead or in combination with IR-light, any conventional drying equipment can be used in the drying step. However, in certain embodiments of the present invention little or no drying is required, e.g. in cases, where only small amounts of surface cross-linkers are applied dissolved in small amounts of solution.

Prior art surface cross-linking has been restricted to carboxylic groups comprised by the polymer chain segments exposed on the surface of the SAP particle. Advantageously, the cross-linking process of the present invention may not be restricted to the carboxyl groups but may also comprise numerous other functional groups and aliphatic groups within the polymer chains of the SAP. Hence, according to the present invention the number of available reaction sites for the surface cross-linking process of the SAP particles may be strongly increased. Therefore, it may be possible to achieve a far more homogenous, uniform surface cross-linking compared to the surface cross-linking known from the art. Furthermore, it may be possible to surface cross-link the SAP to a higher degree than the SAP known from the prior art. This enables to make the SAP particles much stiffer, thus, to more effectively inhibit the gel-blocking effect at any given degree of neutralization.

Surface cross-linking of SAP particles mainly takes place on the surface of the SAP particles. That means that mainly polymer chain segments, which are exposed in the vicinity of the surface of the SAP particles, undergo a cross-linking process, leading to SAP particles with a high degree of cross-linking on their surface while not substantially affecting the inner core of the SAP particles. Hence, the covalent bonds formed directly between said polymer chain segments may be formed mainly on the surface of said superabsorbent particles whereas said core may be substantially free of said covalent bonds.

The UV irradiation for the surface cross-linking can be carried out in a conventional manner with UV lamps having a power between about 50 W and about 2 kW, in one embodiment between about 200 W and about 700 W, and in another embodiment between about 400 W and about 600 W. Irradiation time may be between about 0.1 sec. and about 30 min., in one embodiment between about 0.1 sec. and about 15 min, in another embodiment between about 0.1 sec. and about 5 min and in yet another embodiment between about 0.1 sec. and about 2 min. Commercially available mercury pressure UV-lamps can be used. The choice of the lamp depends on the absorption spectrum of the radical former(s) used. Lamps having a higher power generally permit more rapid cross-linking. The distance between the UV-lamp(s) and the SAP which is to be cross-linked may vary between 5 cm and 15 cm.

Compared to the surface cross-linking known from the prior art, the surface cross-linking according to the present invention may be much quicker. Prior art surface cross-linking reactions carried out under increased temperatures commonly take up to 45 minutes. This time consuming process step renders the manufacturing process of SAP particles less economic than desirable. On the contrary, the cross-linking process according to the present invention can be carried out very quickly and hence, strongly adds to a much more efficient and economic overall manufacturing process.

Furthermore, as the surface cross-linking reaction proceeds quickly, the surface cross-linking molecules applied on the surface of the SAP particles may have less time to penetrate inside the SAP particles. As a result, the surface cross-linking process may be restricted to the surface of the SAP particles and may avoid undesired further cross-linking reactions inside the SAP particles.

Another advantage of the present invention refers to the neutralization step. $\alpha,\beta$-unsaturated carboxylic acid monomers are often neutralized prior to the polymerization step (pre-neutralization). Compounds, which may be useful to neutralize the acid groups of the monomers, are typically those, which will sufficiently neutralize the acid groups without having a detrimental effect on the polymerization process. Such compounds include alkali metal hydroxides, alkali metal carbonates and bicarbonates. The material used for neutralization of the monomers may be sodium or potassium hydroxide or carbonate. The neutralizing compound may be added to an aqueous solution comprising the $\alpha,\beta$-unsaturated carboxylic acid monomers (pre-neutralization). As a result, the carboxyl groups comprised by the $\alpha,\beta$-unsaturated carboxylic acid monomers may be at least partially neutralized. Consequently,—after the polymerization step—also the carboxyl groups comprised by the $\alpha,\beta$-unsaturated carboxylic acid of the polymer may be at least partially neutralized. In case sodium hydroxide is used, neutralization may result in sodium acrylate, which dissociates in water into negatively charged acrylate monomers and positively charged sodium ions.

If the final SAP particles are in the swollen state, after they absorb aqueous solution, the sodium ions may be freely movable within the SAP particles. In absorbent articles, such as diapers or training pants, the SAP particles typically absorb urine. Compared to distilled water, urine comprises a relatively high amount of salt, which at least partly may be present in dissociated form. The dissociated salts comprised by the urine may make absorption of liquid into the SAP particles more difficult, as the liquid has to be absorbed against an osmotic pressure caused by the ions of the dissociated salts. The freely movable sodium ions within the SAP particles may strongly facilitate the absorption of liquid into the particles, because they may reduce the osmotic pressure. Therefore, a high degree of neutralization can largely increase the capacity of the SAP particles and the speed of liquid absorption.

The surface cross-linkers known in the art react with the carboxyl groups of the polymer. Hence, the degree of neutralization has to be balanced with the need to surface cross-link, because both process steps make use of the carboxyl groups.

According to the present invention, the surface cross-linking reaction using radical formers and forming direct covalent bonds between polymer chain segments is not restricted to carboxyl groups but further comprises other groups within the polymer chain segment such as aliphatic groups. Therefore, it may be possible to neutralize the monomers to a larger degree without significantly diminishing the possibility of later surface cross-linking.

According to the present invention, the carboxyl groups comprised by the $\alpha,\beta$-unsaturated carboxylic acid monomers may be at least about 50% neutralized, in one embodiment at least about 70% neutralized, in another embodiment at least about 75% neutralized and in yet another embodiment between about 75% and about 95% neutralized. Hence, also the carboxyl groups comprised by the $\alpha,\beta$-unsaturated carboxylic acid of the polymer may be at least about 50% neutralized, in one embodiment at least about 70% neutralized, in another embodiment at least about 75% neutralized and in yet another embodiment between about 75% and about 95% neutralized.

A still further advantage of the present invention may be the reduction of undesired side-reactions during the surface cross-linking process. Surface cross-linking known from the prior art requires increased temperatures, commonly around or above 150°. At these temperatures, not only the surface cross-linking reaction is achieved, but also a number of other reactions take place, e.g. anhydrate-formation within the polymer or dimer cleavage of dimers previously formed by the acrylic acid monomers. These side-reactions are highly undesired, because they result in SAP particles with decreases capacity.

As the surface cross-linking process according to the present invention does not necessarily need increased temperatures but can also be carried out at moderate temperatures using electromagnetic irradiation, such as UV irradiation, those side-reactions may be substantially eliminated. According to the present invention, the surface cross-linking reaction using radical formers and electromagnetic irradiation can be accomplished at temperatures of less than about 100° C., in one embodiment at temperatures less than about 80° C., in another embodiment at temperatures less than about 50° C., in yet another embodiment at temperatures less than about 40° C., and in a further embodiment at temperatures between about 20° C. and about 40° C.

At elevated temperatures around or above 150° C. commonly applied in the surface cross-linking process known from the prior art, the SAP particles sometimes change their colour from white to yellowish. As according to the surface cross-linking process of the present invention, it may be possible to carry out the surface cross-linking process under moderate temperatures, the problem of colour degradation of the SAP particles may be strongly reduced.

In embodiments of to the present invention using radical formers, one radical former can be selected or, alternatively, two or more different radical formers can be applied.

As a further alternative, one or more radical former can be applied together with one or more thermally activated surface cross-linkers, e.g. 1,4-butandiol. In this embodiment, the SAP particles may comprise carboxyl groups wherein at least some of the carboxyl groups may be at least partially exposed on the outer surface of the SAP particles and wherein the thermally activated surface cross-linker may be covalently bound to at least a part of the carboxyl groups at least partially exposed on the surface of said superabsorbent polymer particles.

In case a radical former is used together with a thermally activated surface cross-linker, both UV irradiation and increased temperatures (above 140° C.) may be necessary for the surface cross-linking process.

The radical former may be used in a liquid solution, and may further be used in an aqueous solution.

To obtain SAP particles with evenly distributed surface cross-linking, the radical former may be distributed evenly on the SAP particle prior to or during UV irradiation. Therefore, the radical former may be applied by spraying onto the SAP particles.

However, the present invention is not restricted to surface cross-linking of SAP particles. It may be possible to directly covalently cross-link polymer chain segments well before the SAP particles have been formed. For example, the radical former can be applied to polymer chains formed from polymerization reaction of the respective monomers before the polymer chains have been cross-linked to each other to form a network. In this embodiment, the cross-linking with the radical former may replace the cross-linking processes known in the art.

Alternatively, the cross-linking according to the present invention can be carried out in addition to known cross-linking process, either prior to the known processes, simultaneously or afterwards.

In these embodiments the radical former may not be applied to SAPs, which have been formed into particles. Consequently, if the polymer is transformed into SAP particles, the direct covalent cross-links between the polymer chain segments may not be restricted mainly to the surface of the SAP particles, but the direct covalent bonds between polymer chain segments will be present throughout the SAP particles, possibly the direct covalent bonds may be distributed homogeneously throughout the SAP particles.

Alternatively, the direct covalent bonds between polymer chain segments may be distributed in-homogeneously throughout the SAP particle. For example, it may be possible to mix different polymers comprising different polymer chain segments. In this case, the different polymer chains may be cross-linked (directly or indirectly by a process known in the art) to a different degree or polymers chains in certain regions of the SAP particles may not be cross-linked at all.

It is also possible to mix different polymers for forming the SAP particles comprising different polymer chain segments. In this case, the different polymers may comprise mixtures of different homopolymers, copolymers and/or block polymers.

However, all such SAP particles comprising direct covalent bonds throughout the SAP particles may undergo surface cross-linking. In this instance, the surface cross-linking may be achieved by subjecting the SAP particles to the radical former of the present invention, by subjecting them to a surface cross-linking process known in the art or by a combination of both.

Absorbent Articles

The SAP particles of the present invention may be applied in absorbent cores of absorbent articles. As used herein, absorbent article refers to devices that absorb and contain liquid, and more specifically, refers to devices that are placed against or in proximity to the body of the wearer to absorb and contain the various exudates discharged from the body. Absorbent articles include but are not limited to diapers, adult incontinent briefs, diaper holders and liners, sanitary napkins and the like.

Absorbent articles of the present invention may be diapers. As used herein, "diaper" refers to an absorbent article generally worn by infants and incontinent persons about the lower torso.

Absorbent articles suitable for the present invention may comprise an outer covering including a liquid pervious topsheet, a liquid impervious backsheet and an absorbent core generally disposed between the topsheet and the backsheet. The absorbent core may comprise any absorbent material that is generally compressible, conformable, non-irritating to the wearer's skin, and capable of absorbing and retaining liquids such as urine and other certain body exudates. In addition to the SAP particles of the present invention, the absorbent core may comprise a wide variety of liquid-absorbent materials commonly used in disposable diapers and other absorbent articles such as comminuted wood pulp, which is generally referred to as air felt.

Exemplary absorbent structures for use as the absorbent assemblies are described in U.S. Pat. No. 5,137,537 entitled "Absorbent Structure Containing Individualized, Polycarboxylic Acid Crosslinked Wood Pulp Cellulose Fibers" which issued to Herron et al. on Aug. 11, 1992; U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994; U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; U.S. Pat. No. 5,397,316 entitled "Slitted Absorbent Members For Aqueous Body Fluids Formed Of Expandable Absorbent Materials" issued to LaVon et al. on Mar. 14, 1995; and U.S. Pat. No. 5,625,222 entitled "Absorbent Foam Materials For Aqueous Fluids Made From high In al. on Jul. 22, 1997.

Furthermore, the SAP particles of the present invention can be applied as absorbent materials. The SAP particles of the present invention may be present in amounts of at least about 50% by weight of the whole absorbent core, in another embodiment at least about 60%, in yet another embodiment at least about 75% and in a further embodiment at least about 90% by weight of the whole absorbent core.

Methods

Ether Extraction:

After photolysis, the reaction products are subjected to an ether extraction. 10 ml of commercially available, dry (≤0.005% water) diethyl ether is added to the reaction product after photolysis, these samples are magnetically stirred for 10 min, then centrifuged for 5 minutes at room temperature. The ether phase is removed with an Eppendorf pipette for further analysis, e.g. for NMR analysis.

NMR Spectroscopy:

For Nuclear Magnetic Resonance Spectroscopy, NMR, either deuterated trichlormethane, $CDCl_3$, or deuterated Methylenenchloride, $CD_2Cl_2$ is used as solvent for the ether extracts. For example a Bruker Avance 300 MHz NMR spectrometer with 7.05 T Oxford super conducting magnet (54 mm bore) and gradient shimming, controlled using a PC/NT Pentium III 750 MHz computer, can be used. For example a 5 mm four-nucleus probe observable for $^1H$, $^{13}C$, $^{19}F$ and $^{31}P$ with z-gradient, variable temperature capability (—150° C. to +200° C.) and boron-free glass insert can be used. Respective $^1$H, $^{13}$C, $^{19}$F spectra are acquired by standard high-resolution (solution) NMR techniques well know to the person skilled in the art.

Photolysis:

200 mg of PAA is mixed with 20 mg of the respective radical former either in the dry state or solved/suspended in 1.5 ml of water. Photolysis is carried out for either 10 or 60 minutes with a 450 W medium pressure Hg lamp as UV source using a pyrex filter to cut out light below a wavelength of 300 nm. Such lamp mostly generates light at a wavelength of 365 nm. All samples are degassed prior to photolysis by either pumping to $10^{-5}$ torr or three freeze-pumping-thaw cycles.

All documents cited in the Detailed Description of the Invention, are, in relevant part, in-corporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. Superabsorbent polymer comprising polymer chains comprising polymer chain segments, wherein at least a part of said polymer chain segments are cross-linked to each other only through direct covalent bonds between said polymer chain segments wherein said direct covalent bonds do not comprise intermediate atoms including atoms comprised by a cross-linking molecule, and are formed between a carbon atom in the backbone of a first polymer chain and a carbon atom of a second polymer chain, wherein the polymer chain segments are a) the part of the polymer chains located between two neighboring, existing cross-links or b) the part of the polymer chains between sites wherein the polymer chain is branched, and wherein said superabsorbent polymer is formed into a superabsorbent polymer particle comprising a surface and a core and wherein said covalent bonds formed directly between said polymer chain segments are formed on the surface of said superabsorbent particles whereas said core is substantially free of said covalent bonds, and wherein said polymer chain segments are block copolymer segments.

2. Superabsorbent polymer according to claim 1, wherein said polymer chain segments comprise polycarboxylic acid units and wherein said covalent bonds are formed directly between said polycarboxylic acid units of said polymer chain segments.

3. Superabsorbent polymer according to claim 2, wherein said polycarboxylic acrylic acid units are selected from the group consisting of polyacrylic acid units, polymethacrylic acid units and combinations thereof.

4. Superabsorbent polymer according to claim 2, wherein said polycarboxylic acid units are at least partially neutralized.

5. Superabsorbent polymer according to claim 1, wherein said superabsorbent polymer is formed into a superabsorbent polymer particle and wherein the direct covalent bonds are solely formed intraparticulate.

6. Superabsorbent polymer according to claim 1, wherein said covalent bonds are induced by electromagnetic irradiation without the use of any radiation activatable radical formers.

* * * * *